(12) United States Patent
Coniglio et al.

(10) Patent No.: US 6,248,729 B1
(45) Date of Patent: Jun. 19, 2001

(54) COMBINATION OF AN ADP-RECEPTOR BLOCKING ANTIPLATELET DRUG AND ANTIHYPERTENSIVE DRUG AND A METHOD FOR PREVENTING A CEREBRAL INFARCTION EMPLOYING SUCH COMBINATION

(75) Inventors: Anthony A. Coniglio, Branchburg; Francis R. Plat, Skillman, both of NJ (US); Melvin S. Blumenthal, Yardley, PA (US)

(73) Assignees: Bristol-Myers Squibb Co., Princeton, NJ (US); Sanofi-Synthelabo, Paris (FR)

( * ) Notice: Subject to any disclaimer, the term of this patent is extended or adjusted under 35 U.S.C. 154(b) by 0 days.

(21) Appl. No.: 09/328,812

(22) Filed: Jun. 9, 1999

Related U.S. Application Data

(60) Provisional application No. 60/089,650, filed on Jun. 17, 1998.

(51) Int. Cl.[7] ........................ A61K 31/675; A61K 31/55; A61K 31/44; A61K 31/41; A61K 31/415; A61K 31/40

(52) U.S. Cl. ........................ 514/85; 514/214.02; 514/301; 514/381; 514/397; 514/423

(58) Field of Search .................. 514/301, 214.02, 514/423, 85, 381, 397

(56) References Cited

U.S. PATENT DOCUMENTS

| | | |
|---|---|---|
| 4,529,596 | 7/1985 | Aubert et al. . |
| 4,591,592 | 5/1986 | Chowhan ............................ 514/301 |
| 4,847,265 | 7/1989 | Badore et al. . |
| 5,225,420 | 7/1993 | Cazenave et al. . |
| 5,270,317 | 12/1993 | Bernhart et al. . |
| 5,362,727 | 11/1994 | Robl ..................................... 514/214 |
| 5,366,973 | 11/1994 | Flynn et al. ......................... 514/221 |
| 5,508,272 | 4/1996 | Robl ..................................... 514/80 |
| 5,525,723 | 6/1996 | Robl ..................................... 540/521 |
| 5,576,328 | 11/1996 | Herbert et al. . |
| 5,661,150 | 8/1997 | Shirasaki ............................. 514/252 |

FOREIGN PATENT DOCUMENTS

| | | |
|---|---|---|
| 481522 | 4/1992 | (EP) . |
| 534363 | 3/1993 | (EP) . |
| 534396 | 3/1993 | (EP) . |
| 534492 | 3/1993 | (EP) . |
| 595610 | 5/1994 | (EP) . |
| 599444 | 6/1994 | (EP) . |
| 629627 | 12/1994 | (EP) . |
| 93/16103 | 8/1993 | (WO) . |
| 94/10193 | 5/1994 | (WO) . |
| WO97/29753 | 8/1997 | (WO) . |
| WO98/11896 | 3/1998 | (WO) . |
| 00/16773 | 3/2000 | (WO) . |

OTHER PUBLICATIONS

Wityk et al., Critical Care Medicine, vol. 22, No. 8, p. 1278–1293 (1994).
Cazaubon et al., Journal of Pharm And Exper Therapeutics, vol. 265, No. 2, p. 826–834 (1993).
Herbert et al., European Journal of Pharmacology, vol. 251, p. 143–150 (1994).
Chatelain et al., Eur. J. Med. Chem., vol. 32, p. 687–707 (1997).
Adams et al., Journal of Cardiac Failure, vol. 5, No. 4, p. 357–382 (1999).

*Primary Examiner*—Raymond Henley, III
(74) *Attorney, Agent, or Firm*—Burton Rodney; Stephen B. Davis

(57) ABSTRACT

A method is provided for preventing a cerebral infarction by administering to a patient a combination of an ADP-receptor blocking antiplatelet drug, such as clopidogrel, in combination with an antihypertensive agent such as an angiotensin AII antagonist (for example, irbesartan), an ACE inhibitor (for example, fosinopril) or a NEP/ACE inhibitor such as omapatrilat.

25 Claims, No Drawings

COMBINATION OF AN ADP-RECEPTOR BLOCKING ANTIPLATELET DRUG AND ANTIHYPERTENSIVE DRUG AND A METHOD FOR PREVENTING A CEREBRAL INFARCTION EMPLOYING SUCH COMBINATION

Priority is claimed from U.S. application Ser. No. 60/089,650 filed Jun. 17, 1998.

FIELD OF THE INVENTION

The present invention relates to a novel combination of an ADP-receptor blocking antiplatelet drug, such as clopidogrel, and an antihypertensive drug, for example, an angiotensin II antagonist such as irbesartan, or an ACE inhibitor such as fosinopril, or a NEP/ACE inhibitor such as omapatrilat, and to a method for preventing or inhibiting onset of a cerebral infarction employing such combination.

BACKGROUND OF THE INVENTION

Ticlopidine hydrochloride is disclosed in U.S. Pat. No. 4,591,592 as a platelet aggregation inhibitor, is marketed in the U.S. under the name Ticlid® by Roche Laboratories, and has the chemical name 5-[(2-chlorophenyl)methyl]-4,5,6,7-tetrahydrothieno[3,2-c]pyridine hydrochloride and the structure

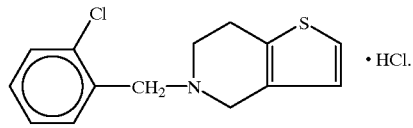

Clopidogrel is a thieno-[3,2-c]pyridine derivative which has the chemical name methyl (4)-(S)-α-(o-chloro-phenyl)-6,7-dihydrothieno[3,2-c]pyridine-5-acetate and the formula

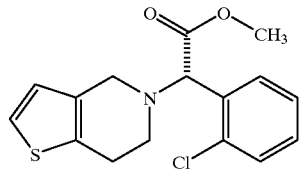

including pharmaceutically acceptable acid addition salts thereof, preferably the hydrogen sulfate salt, and is disclosed in U.S. Pat. Nos. 4,529,596 to Aubert et al and U.S. Pat. No. 4,847,265 to Badorc et al as having blood platelet aggregation inhibiting activity and anti-thrombotic activity and thus useful in inhibiting or preventing arterial and venous thrombosis.

U.S. Pat. No. 5,576,328 to Herbert et al discloses that clopidogrel may be employed in secondary prevention of ischemic events such as myocardial infarction, unstable or stable angina, acute reocclusion after percutaneous transluminal coronary angioplasty (PTCA), restenosis after PTCA, thrombotic stroke, transient ischemic attack, reversible ischemic neurological deficit, and intermittent claudication.

The above Aubert et al, Badorc et al and Herbert et al patents are incorporated herein by reference.

WO 97/29753 published Aug. 21, 1997, discloses a pharmaceutical composition containing clopidogrel and aspirin.

Bernhart et al in U.S. Pat. No. 5,270,317 disclose a series of N-substituted heterocyclic derivatives which possess angiotensin II antagonist activity. Bernhart et al disclose that such compounds can be used in the treatment of various cardiovascular complaints, especially hypertension, heart failure, and venous insufficiency, as well as in the treatment of glaucoma, diabetic retinopathy and various complaints of the central nervous system. It is also disclosed that such compound can be used in combination with other active agents such as tranquilizers, beta-blocking compounds, a calcium antagonist, or a diuretic.

Selective neutral endopeptidase inhibitors are taught by Delaney et al in U.S. Pat. Nos. 4,722,810 and 5,223,516 and the use of selective neutral endopeptidase inhibitors alone or in combination with angiotensin converting enzyme inhibitors to treat hypertension are disclosed by Delaney et al U.K. Patent Application 2,207,351 and by Haslanger et al in U.S. Pat. No. 4,749,688. The treatment of congestive heart failure by administration of a combination of a selective neutral endopeptidase inhibitor and an angiotensin converting enzyme inhibitor is disclosed by Seymour in U.S. Pat. No. 5,225,401.

Compounds possessing both neutral endopeptidase and angiotensin converting enzyme inhibition activity are disclosed by Flynn et al in U.S. Pat. No. 5,366,973, European Patent Application 481,522 and PCT Patent Applications WO 93/16103, and WO 94/10193, Warshawsky et al European Patent Applications 534,363, 534,396 and 534,492, Fournie-Zaluski European Patent Application 524,553, Barrish et al European Patent Application 599,444, Karanewsky European Patent Application 595,610, Robl et al, European Patent Application 629,627, Robl U.S. Pat. No. 5,362,727 and U.S. patent application Ser. No. 153,854 filed Nov. 18, 1993, now U.S. Pat. No. 5,525,723.

DESCRIPTION OF THE INVENTION

In accordance with the present invention, a method for preventing or inhibiting onset of a cerebral infarction in mammals is provided wherein an ADP-receptor blocking antiplatelet drug, such as clopidogrel, in combination with an antihypertensive drug is administered in therapeutically effective amounts to inhibit onset of a cerebral infarction (also known as a thrombotic stroke).

In addition, in accordance with the present invention, a novel combination is provided which includes an ADP-receptor blocking antiplatelet drug, such as clopidogrel, and an antihypertensive drug.

ADP-receptor blocking drugs which may be used in the combination and method of the invention include clopidogrel, ticlopidine and the like.

Antihypertensive drugs, which may be used in the combination and method of the invention in combination with the ADP-receptor blocking antiplatelet drug include angiotensin II antagonists, angiotensin converting enzyme (ACE) inhibitors or NEP/ACE inhibitors.

It is believed that the combination of an ADP-receptor blocking antiplatelet drug and the antihypertensive drug, which works by a mechanism other than inhibition of ADP-induced platelet aggregation, is a surprising and unique concept in treating diseases involved with platelet aggregation, thrombus formation and ischemic events, in that the combination may provide additional antiplatelet aggregation, antiischemic and anti-thrombus effects over that which may be obtained using each of the components of the combination alone. It may be expected that reduced levels of each of the ADP-receptor blocking antiplatelet drug and antihypertensive drug may be employed to achieve desired results, albeit with reduced side effects and at reduced cost of goods.

DETAILED DESCRIPTION OF THE INVENTION

The following definitions apply to the terms as used throughout this specification, unless otherwise limited in specific instances.

The term "ADP-receptor blocking antiplatelet drug" refers to drugs which inhibit ADP-induced platelet aggregation via platelet ADP-receptor blocking including clopidogrel and/or ticlopidine and do not include drugs such as aspirin which inhibit platelet aggregation by other mechanisms.

The term "clopidogrel" as employed herein includes clopidogrel in its free acid form, esters thereof including the acetate and/or all pharmaceutically acceptable salts thereof, including the hydrogen sulfate salt.

The term "ticlopidine" as employed herein includes all pharmaceutically acceptable salts of ticlopidine, including the hydrochloride salt thereof.

The term "cerebral infarction" as employed herein refers to primary or secondary thrombotic stroke.

It is to be understood that the term "antihypertensive drug" refers to various classes of antihypertensive agents including angiotensin II antagonists, ACE inhibitors and NEP/ACE inhibitors which contribute, with the antiplatelet drug, to inhibit onset of primary or secondary cerebral infarction.

The combination of the ADP-receptor blocking antiplatelet drug, such as clopidogrel or ticlopidine, and the antihypertensive drug will be employed in a weight ratio to each other of within the range of from about 1000:1 to about 0.001:1, and preferably from about 0.05:1 to about 100:1.

The angiotensin II receptor antagonist (also referred to herein as angiotensin II antagonist or AII antagonist) suitable for use herein includes, but is not limited to, irbesartan, including salts thereof such as the K and Na salts thereof (disclosed in U.S. Pat. No. 5,270,317 to Bernhart et al), losartan, valsartan, telmisartan, candesartan, tasosartan or eprosartan, with irbesartan or losartan being preferred.

The angiotensin converting enzyme inhibitor which may be employed herein includes those containing a mercapto (-S-) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol. 10:131 (1983); as well as pivopril, that is

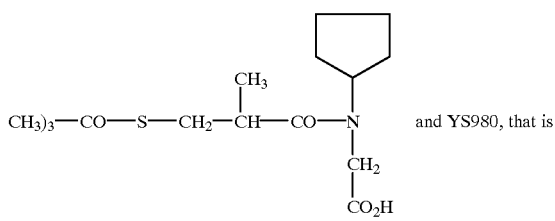

and YS980, that is

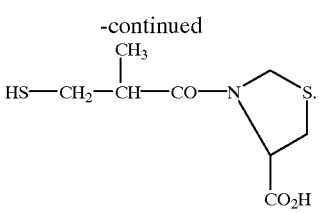

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)-phosphinyl]oxy]-1-oxohexyl]-L-proline or (ceronapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European Patent Nos. 80822 and 60668; Chugai's MC-838 disclosed in CA. 102:72588v and Jap. J. Pharmacol. 40:373 (1986); Ciba-Geigy's CGS 14824 (3-([1-ethoxycarbonyl-3-phenyl-(1S)-propyl]amino)-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechst) disclosed in Eur. Patent No. 79-022 and Curr. Ther. Res. 40:74 (1986); Ru 44570 (Hoechst) disclosed in Arzneimittelforschung 35:1254 (1985), cilazapril (Hoffman-LaRoche) disclosed in J. Cardiovasc. Pharmacol. 9:39 (1987); R₀ 31-2201 (Hoffman-LaRoche) disclosed in FEBS Lett. 165:201 (1984); lisinopril (Merck), indalapril (delapril) disclosed in U.S. Pat. No. 4,385,051; indolapril (Schering) disclosed in J. Cardiovasc. Pharmacol. 5:643, 655 (1983), spirapril (Schering) disclosed in Acta. Pharmacol. Toxicol. 59 (Supp. 5):173 (1986); perindopril (Servier) disclosed in Eur. J. Clin. Pharmacol. 31:519 (1987); quinapril (Warner-Lambert) disclosed in U.S. Pat. No. 4,344,949 and CI 925 (Warner-Lambert) ([3S-[2[R(*)R(*)]] 3R(*)]-2-[2-[[1-(ethoxy-carbonyl)-3-phenylpropyl]amino[-1-oxopropyl]-1,2,3,4-tetrahydro-6,7-dimethoxy-3-isoquinolinecarboxylic acid HCl) disclosed in Pharmacologist 26:243, 266 (1984), WY-44221 (Wyeth) disclosed in J. Med. Chem. 26:394 (1983).

Preferred ACE inhibitors are fosinopril, as well as captopril, enalapril, lisinopril, quinapril, benazapril, trandolapril, fentiapril, ramipril, and moexipril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. Nos. 5,508,272, 5,362,727, 5,366,973, 5,225,401, 4,722,810, 5,223,516, 5,552,397, 4,749,688, 5,504,080, 5,612,359, and 5,525,723 and European Patent Applications 0481,522, 0534363A2, 534,396 and 534,492, Preferred are those NEP/ACE inhibitors which are designated as preferred in the above U.S. patents which are incorporated herein by reference. Especially preferred is the angiotensin II antagonist losartan or irbesartan, or EP/ACE inhibitor omapatrilat (disclosed in U.S. Pat. No. 5,508,272), in combination with clopidogrel.

The ADP-receptor blocking antiplatelet drug will be employed in combination with an ACE inhibitor or AII antagonist, or NEP/ACE inhibitor, in a weight ratio to ACE inhibitor or AII antagonist or NEP/ACE inhibitor of within the range from about 0.1:1 to about 50:1, and preferably from about 0.2:1 to about 20:1.

It will also be appreciated that the drugs or compounds employed herein in accordance with the present invention may be employed in conjunction or combination with one or more known therapeutic agents for preventing or treating cerebral infarction, such as, for example, but not limited to cholesterol lowering drugs such as including HMG CoA reductase inhibitors preferably pravastatin, lovastatin, simvastatin, atovastatin, fluvastatin and cerivastatin.

Other cholesterol lowering drugs suitable for use herein include, but are not limited to, antihyperlipoproteinemic agents such as fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Polidexide®), as well as clofibrate, lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

Aspirin may optionally be included in the combination of the invention.

In carrying out the method of the present invention, the ADP-receptor blocking antiplatelet drug in combination with the antihypertensive drug may be administered to mammalian species, such as monkeys, dogs, cats, rats, humans, etc., and, as such, may be incorporated in a conventional systemic dosage form, such as a tablet, capsule, elixir or injectable. The above dosage forms will also include the necessary carrier material, excipient, lubricant, buffer, antibacterial, bulking agent (such as mennitol), antioxidants (ascorbic acid of sodium bisulfite) or the like. Oral dosage forms are preferred, although parenteral forms are quite satisfactory as well.

The dose administered must be adjusted according to age, weight and condition of the patient, as well as the route of administration, dosage form and regimen and the desired result.

Clopidogrel will be employed in an oral daily dosage within the range from about 10 to about 1000 mg, and preferably from about 25 to about 600 mg, and most preferably, from about 50 to 100 mg.

Ticlopidine may be employed in a daily dosage as set out in the 1997 PDR (250 mg bid) although daily dosages from about 10 to about 1000 mg, preferably 25 to about 800 mg may be employed in accordance with the present invention.

The or dual acting neutral endopeptidase and angiotensin converting enzyme inhibitor can be administered at a dosage range from about 0.03 to about 1000 mg per kg of body weight per day with a dosage range of from about 0.3 to about 300 mg per kg of body weight per day being preferred. The angiotensin II antagonist or ACE inhibitor can be administered at a dosage range from about 0.001 to about 75 mg per kg of body weight with a dosage range of from about 0.1 to about 15 mg per kg of body weight being preferred or as directed in the Physicians Desk Reference 1998 (52 Ed.).

For oral administration, a satisfactory result my be obtained employing the HMG CoA reductase inhibitor in dosages employed, for example, for lovastatin, pravastatin, simvastatin, fluvastatin, lovastatin, atorvastatin or cerivastatin, as indicated in the Physician's Desk Reference 1998 (52 Ed.), such as in an amount within the range of from about 0.1 to 2000 mg, and preferably from about 0.2 to about 200 mg.

A preferred oral dosage form, such as tablets or capsules, will contain clopidogrel or ticlopidine in an amount from about 10 to about 500 mg, and the antihypertensive agent in an amount of from about 0.1 to about 1000 mg.

The other serum cholesterol lowering drugs when present will be employed in dosages normally employed as indicated in the Physician's Desk Reference, for each of such agents such as in an amount within the range from about 0.1 mg to about 7500 mg and preferably from about 2 mg to about 4000 mg.

Where present, the aspirin (employed with the ADP-receptor blocking antiplatelet drug and antihypertensive agent) will be employed in daily dosages within the range from about 1 mg to about 500 mg, preferably from about 20 mg to about 100 mg, and in a weight ratio to the ADP receptor blocking antiplatelet drug within the range from about 0.02:1 to about 1000:1, preferably from about 0.04:1 to about 20:1.

The ADP-receptor blocking antiplatelet drug and the antihypertensive agent, and optionally drugs for preventing or treating cerebral infarction may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

Tablets of various sizes can be prepared, e.g., of about 2 to 2000 mg in total weight, containing one or both of the active substances in the ranges described above, with the remainder being a physiologically acceptable carrier of other materials according to accepted pharmaceutical practice. These tablets can, of course, be scored to provide for fractional doses. Gelatin capsules can be similarly formulated.

Liquid formulations can also be prepared by dissolving or suspending one or the combination of active substances in a conventional liquid vehicle acceptable for pharmaceutical administration so as to provide the desired dosage in one to four teaspoonsful.

Such dosage forms can be administered to the patient on a regimen of one to four doses per day.

According to another modification, in order to more finely regulate the dosage schedule, the active substances may be administered separately in individual dosage units at the same time or carefully coordinated times. The respective substances can be individually formulated in separate unit dosage forms in a manner similar to that described above.

Fixed combinations of the ADP-receptor blocking antiplatelet drug and the antihypertensive drug and optionally components are more convenient and are preferred, especially in tablet or capsule form for oral administration.

In formulating the compositions, the active substances, in the amounts described above, are compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, aspartame, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

Some of the active substances described above form commonly known, pharmaceutically acceptable salts such as alkali metal and other common basic salts or acid addition salts, etc. References to the base substances are therefore intended to include those common salts known to be substantially equivalent to the parent compound.

The formulations as described above will be administered for a prolonged period, that is, for as long as the potential for cerebral infarction continues. Sustained release forms of such formulations which may provide such amounts biweekly, weekly, monthly and the like may also be employed. A dosing period of at least three days are required to achieve minimal benefit.

The following Examples represent preferred embodiments of the present invention.

Formulations suitable for oral administration for inhibiting platelet aggregation and thrombus formation are prepared as described below.

EXAMPLE 1

Capsules are prepared each containing 75 mg clopidogrel (as described below) and 150 mg irbesartan (as described in the 1998 PDR)

| Ingredient | Example 1 Amount (mg/Capsule) |
| --- | --- |
| Clopidogrel hydrogen sulfate | 75 |
| Lactose, Hydrous, NF ca. | 108 |
| Microcrystalline Cellulose, ca. NF | 13 |
| Pregelatinized Starch, NF | 10.5 |
| Polyethylene glycol 6000 NF | 7.5 |
| Hydrogenated castor oil, NF | 3.3 |

The above clopidogrel tablet is prepared by blending anhydrous lactose, clopidogrel hydrogen sulfate, pregelatinized starch, and polyethylene glycol 6000 in a bin-type blender for about 15 minutes at 7 rpm.

The blended mix is then screened (1.25 mm screen) and blended for about 30 minutes at 7 rpm in a bin-type blender. The blend is compacted using a roller compactor fitted with milling equipment. The milled granulation which contains particles ranging from 1 mm to less than 20 mm is blended with microcrystalline cellulose (screen through 1.25 mm screen) and hydrogenated castor oil in a bin-type blender for about 30 minutes at 7 rpm. The blend is compressed into 240 mg tablets.

The clopidogrel tablets and 150 mg irbesartan tablets are ground into powders and filled into a single capsule.

EXAMPLE 2

Capsules each containing 75 mg clopidogrel hydrogen sulfate (tablets as described in Example 1) and 20 mg fosinopril (tablets as described in 1998 PDR) are prepared by grinding up the clopidogrel tablet and fosinopril tablet and filling the resulting powders into a single capsule.

EXAMPLES 3 and 4

Formulations suitable for oral administration for inhibiting platelet aggregation and thrombus formation are prepared as described below.

Capsules each containing 75 mg clopidogrel hydrogen sulfate (prepared as per Example 1) and about 10 mg omapatrilat (Example 3), and about 20 mg omapatrilat (Example 4) are produced from the following ingredients.

| Ingredient | Example 3 Amount (mg/ Capsule) | Example 4 Amount (mg/ Capsule) |
| --- | --- | --- |
| Clopidogrel (Example 1 formulation) | 75 | 75 |
| Omapatrilat | 10 | 20 |
| Lactose, Hydrous, NF | ca. 151.1 | ca. 99.9 |
| Microcrystalline Cellulose, NF | 50.0 | 50.0 |
| Pregelatinized Starch, NF | 25.0 | 25.0 |
| Sodium Starch Glycolate, NF | 12.5 | 12.5 |
| Colloidal Silicon Dioxide, NF | 5.0 | 5.0 |
| Magnesium Stearate, NF | 0.6 | 0.6 |
| Purified Water, USP or Water for Injection, USP | q.s. | q.s. |
| | q.s. | q.s. |
| Gray, Opaque, Size #0 Capsule Shell | One Capsule | One Capsule |

The omapatrilat, and colloidal silicon dioxide are blended in a suitable blender with lactose hydrous, microcrystalline cellulose, pregelatinized starch and a portion of sodium starch glycolate. The resulting blend is wet granulated with water. The wet granulation is dried in a suitable dryer. The remaining portion of sodium starch glycolate is added to the granulation and mixed therein. Magnesium stearate is added to the granulation and mixed therein. The resulting blend is filled into capsules together with ground up clopidogrel tablets.

What is claimed is:

1. A pharmaceutical composition comprising an ADP-receptor blocking antiplatelet drug and an angiotensin II antagonist.

2. A pharmaceutical composition comprising an ADP-receptor blocking antiplatelet drug and an ACE inhibitor.

3. A pharmaceutical composition comprising an ADP-receptor blocking antiplatelet drug and a dual NEP/ACE inhibitor.

4. The composition as defined in claim 1 wherein the antiplatelet drug is clopidogrel which is present in a weight ratio to the angiotensin II antagonist which is irbesartan within the range from about 0.001:1 to about 1000:1.

5. The composition as defined in claim 2 wherein the antiplatelet drug is clopidogrel or ticlopidine.

6. The composition as defined in claim 3 wherein the antiplatelet drug is clopidogrel or ticlopidine.

7. The composition as defined in claim 1 wherein the antiplatelet drug is clopidogrel or ticlopidine.

8. The composition as defined in claim 2 wherein the antiplatelet drug is clopidogrel which is present in a weight ratio to the ACE inhibitor which is fosinopril within the range from about 0.001:1 to about 1000:1.

9. The composition as defined in claim 3 wherein the antiplatelet drug is present in a weight ratio to the dual NEP/ACE inhibitor of within the range of from about 0.001:1 to about 1000:1.

10. The composition as defined in claim 1 wherein the angiotensin II antagonist is irbesartan, losartan, telmisartan, valsartan, candesartan, tasosartan or eprosartan and the antiplatelet drug is clopidogrel or ticlopidine.

11. The composition as defined in claim 2 wherein the antiplatelet drug is clopidogrel which is present in a weight ratio to the ACE inhibitor which is ramipril within the range from about 0.001 to 1 to about 1000:1.

12. The composition as defined in claim 3 wherein the antiplatelet drug is clopidogrel which is present in a weight ratio to the dual NEP/ACE inhibitor which is omapatrilat within the range from about 0.001:1 to about 1000:1.

13. The composition as defined in claim 1 wherein the antiplatelet drug is present in a weight ratio to the angiotensin II antagonist of within the range of from about 0.001:1 to about 1000:1.

14. The composition as defined in claim 2 wherein the ACE inhibitor is fosinopril, enalapril, lisinopril, captopril, quinapril, trandolapril, ramipril or benazapril, and the antiplatelet drug is clopidogrel or ticlopidine.

15. The composition as defined in claim 3 wherein the NEP/ACE inhibitor is omapatrilat and the anti-platelet drug is clopidogrel or ticlopidine.

16. A method for preventing or inhibiting or treating a cerebral infarction in a mammalian species, which comprises administering to a patient in need of treatment a therapeutically effective amount of a pharmaceutical composition as defined in claim 1.

17. The method as defined in claim 16 wherein the cerebral infarction is a primary or secondary ischemic event.

18. The method as defined in claim 16 wherein the pharmaceutical composition comprises an angiotensin II antagonist which is irbesartan, losartan, valsartan, candesartan, telmisartan, tasosartan or eprosartan and clopidogrel.

19. A method for preventing or inhibiting or treating a cerebral infarction in a mammalian species, which comprises administering to a patient in need of treatment a therapeutically effect amount of a pharmaceutical composition as defined in claim 2.

20. The method as defined in claim 5 wherein the cerebral infarction is a primary or secondary ischemic event.

21. A method for preventing or inhibiting or treating a cerebral infarction in a mammalian species, which comprises administering to a patient in need of treatment a therapeutically effective amount of a pharmaceutical composition as defined in claim 3.

22. The method as defined in claim 20 wherein the cerebral infarction is a primary or secondary ischemic event.

23. The method as defined in claim 21 wherein the pharmaceutical composition comprises an ACE inhibitor which is fosinopril, enalapril, lisinopril, captopril, quinapril, trandolapril, ramipril or benazapril and clopidogrel.

24. The method as defined in claim 21 wherein the pharmaceutical composition comprises a NEP/ACE inhibitor which is omapatrilat and clopidogrel.

25. The composition as defined in claim 2 wherein the antiplatelet drug is present in a weight ratio to the ACE inhibitor of within the range of from about 0.001:1 to about 1000:1.

* * * * *